United States Patent [19]

Murphy

[11] Patent Number: 5,097,825
[45] Date of Patent: Mar. 24, 1992

[54] TRAUMA PROTECTOR FOR USE IN DRAWING BLOOD

[76] Inventor: Marilyn M. Murphy, 4606 Mountain View Trail, Clarkston, Mich. 48016

[21] Appl. No.: 313,350

[22] Filed: Feb. 21, 1989

Related U.S. Application Data

[63] Continuation of Ser. No. 129,068, Dec. 7, 1987, abandoned.

[51] Int. Cl.⁵ ............................................. A61F 13/06
[52] U.S. Cl. ........................................ 602/65; 2/22; 602/62
[58] Field of Search .................. 128/80 H, 132 R, 155, 128/156, 165, 166, 169, 171, 157, 846, 892, 893, 894; 2/2, 22, DIG. 7

[56] References Cited

U.S. PATENT DOCUMENTS

| | | | |
|---|---|---|---|
| 3,266,058 | 8/1966 | Guttman | 2/239 |
| 3,383,708 | 5/1968 | Pappas | 2/22 |
| 3,407,811 | 10/1968 | Stubbs | 128/166 |
| 3,527,211 | 9/1970 | Baker | 128/166 |
| 4,133,311 | 1/1979 | Karczewski | 128/166 |
| 4,590,932 | 5/1986 | Wilkerson | 128/166 |
| 4,597,395 | 7/1986 | Barlow et al. | 128/166 |
| 4,769,854 | 9/1988 | Williams | 128/80 H |
| 4,841,957 | 6/1989 | Wooten et al. | 128/166 |

FOREIGN PATENT DOCUMENTS 0217452  4/1987  European Pat. Off. ............ 128/166

Primary Examiner—Randall L. Green
Assistant Examiner—Paul Prebilic
Attorney, Agent, or Firm—Gifford, Groh, Sprinkle, Patmore and Anderson

[57] ABSTRACT

A trauma protector for protecting the limb of an infant during a procedure for taking of blood. The trauma protector provided with two pairs of flaps which overlap on the back of the infant's leg and foot to support the foot and ankle and protect the infant's foot and ankle from trauma arising from pressure applied during the procedure to stabilize the ankle of the infant. A support member is removably affixed to the pad in the instep region to further support the foot.

7 Claims, 1 Drawing Sheet

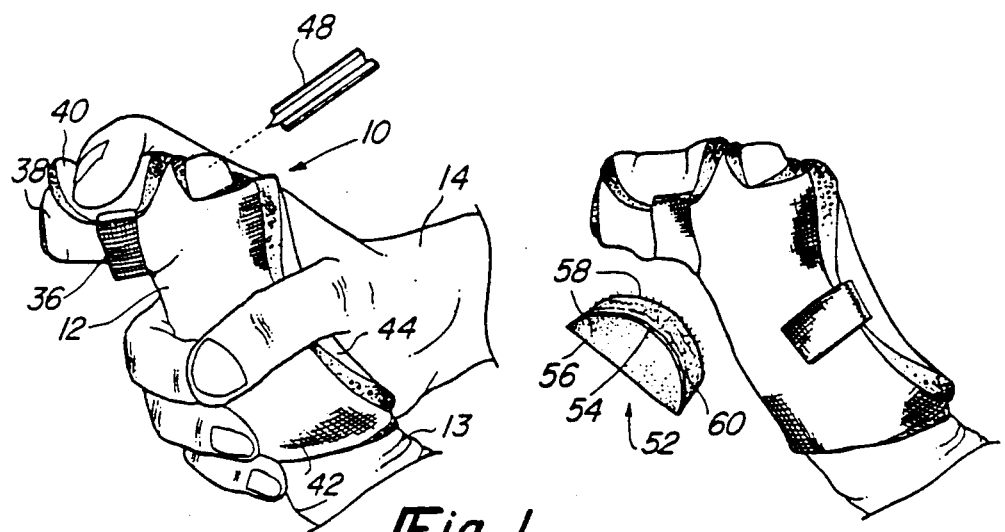
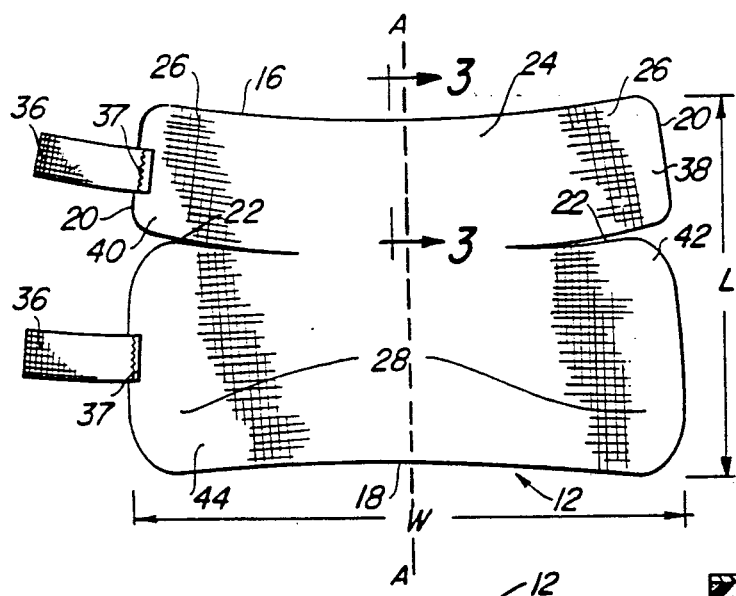
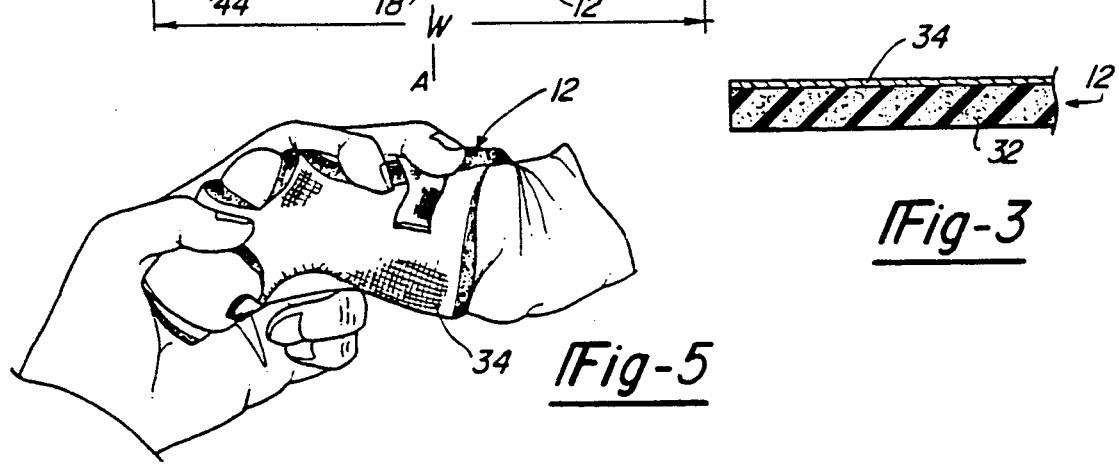

TRAUMA PROTECTOR FOR USE IN DRAWING BLOOD

This is a continuation of co-pending application Ser. No. 129,068 filed on Dec. 7, 1987, abandoned.

BACKGROUND OF THE INVENITON

I. Field of the Invention

The present invention relates to devices for use in protecting a patient from trauma during a procedure for drawing blood and in particular to devices which protect the leg and foot of an infant from trauma during the blood drawing procddure.

II. Description of the Prior Art

It is frequently necessary to draw blood from an infant for use in blood tests and the like. Normally, the blood is drawn from the infant's heel. To withdraw blood, a nurse or technician grasps the foot and leg of the infant in one hand, and inserts a point of a lancet into the infant's heel with an other hand.

However, body tissue of a newborn infant is quite fragile and the infant's skin is frequently dry and scaly. As a result, the hand pressure applied by the technician to the infant's foot and leg frequently produces trauma such as severe bruising and skin loss to the infant. Thus, it would be desirable to reduce the trauma occurring to the infant during a blood withdrawal procedure.

Devices are known in the medical field which stabilize the ankle such as casts and splints and the like. Additionally, many devices are known which protect the ankle from trauma resulting from contact occurring during sports such as hockey, bowling and football; however, none of these devices are suitable for preventing trauma during the withdrawal of blood. Braces, such as disclosed in U.S. Pat. No. 4,278,793 to Mauldin, provide rigid stabilization of the ankle. However, such devices are heavy, cumbersome and not well suited for grasping by the hand of a technician during the taking of blood.

Therefore, it would be desirable to provide a simple and inexpensive trauma protector which protects the infant from trauma during the taking of blood.

SUMMARY OF THE INVENTION

Applicant's invention provides a trauma protector for protecting the limb of an infant during a procedure for drawing blood. Applicant discloses a trauma protector having a foam pad which is secured on the leg and foot of the infant. The foam pad is generally rectangular in shape and has an elongated portion which is adapted to be positioned on the infant's instep and extend from the end of the toes to above the ankle. A pair of first wrap portions and a pair of second wrap portions extend from the elongated portion. The pairs of first and second wrap portions are separated by a pair of slits. The pair of first wrap portions is adapted to extend around the infant's foot and the pair of second wrap portions is adapted to extend around the leg and ankle. The pad, thus, extends over the foot and leg to absorb and disperse the pressure exerted by the hand of the technician. In doing so, the trauma protector prevents bruising of the leg as well as accidental removal of skin from the infant's leg and foot. The slits define an opening extending over the heel to provide access for insertion of a lancet to draw blood. Attachment strips are provided to secure the pairs of first and second wrap portions in position, thereby stabilizing the heel within the pad A support member is provided for mounting to the elongated portion of the pad adjacent to the inner surface of the joint. The support member provides additional stability to the joint and distributes the force of the fingers of the technician to reduce trauma.

It is, therefore, an object of the invention to provide a trauma protector having a foam pad to distribute the force of a technician's hand to protect a limb from truama.

It is a further object of this invention to provide a trauma protector which stabilizes a limb in position for injection or withdrawal of fluid from the limb.

It is another object of the invention to provide a trauma protector which is simply and economically produced.

It is yet another object of the invention to provide a truama protector which is simple and easy to install in position and to remove.

BRIEF DESCRIPTION OF THE DRAWINGS

FIG. 1 is a perspective view of a trauma protector in accordance with the invention in position of the leg and foot of an infant;

FIG. 2 is a top view of a foam pad in an open position in accordance with the invention;

FIG. 3 is a partial side view taken along the lines 3—3 of FIG. 2 showing a cross-sectional view of the foam pad;

FIG. 4 is a perspective exploded view showing a support member detached from the pad; and FIG. 5. is a perspective view of the trauma protector grasped by a technician in an alternative manner than that of FIG. 1 and showing the support member.

DESCRIPTION OF THE PREFERRED EMBODIMENT

As shown in FIG. 1, a trauma protector 10 according to the present invention includes a pad 12 which is positioned about a leg 13 of an infant for use during procedures for injection or removal of fluid such as blood from the infant. The pad 12 is adapted to extend between a hand 14 of a technician and the leg 13 to protect the leg from trauma such as bruising or the removal of skin.

As best shown in FIG. 2, the pad 12 is generally rectangular in shape having a top edge 16, bottom edge 18 and a pair of side edges 20. Each of a pair of slits 22 extend inwardly from each of the pair of side edges 20 to an elongated portion 24. The pair of slits may be formed by any satisfactory method such as with a knife.. The elongated portion 24 has a longitudinal axis shown as A-A in FIG. 2 extending between the top edge 16 and bottom edge 18 of the pad. The pair of slits 22 extend generally in a direction normal to the longitudinal axis of the elongated portion 24 to define a pair of first wrap portions 26 extending from the center porton 24 adjacent the top edge 16 and a pair of second wrap portions 28 extending from the center portion adjacent the bottom edge. The pair of first wrap portions has an inner flap 38 and an outer flap 40. The pair of second wrap portions has an inner flap 42 and an outer flap 44 for a purpose as will be set forth more fully below.

The pad 24 has a length "L" extending between the top edge 16 and the bottom edge 18 of the pad. The length "L" of the pad is approximately 4 to 5 inches and is sufficient to extend from above the ankle to the end of the infant's toes. Thus, the pad covers all portions of the limb which are normally contacted by the hand 14 of the technician during the procedure.

Referring to FIGS. 1 and 2, the pad 12 has a width "W" extending between the pair of side edges 20. The width "W" is greater than the circumference of the leg of the infant so that the pairs of first and second wrap portions extend around the leg to overlap and fully surround the infant's leg 13. The elongated portion 24 extends between the pair of slits 22 a distance equivalent to approximately half the width "W" of the pad 12. The elongated portion 24, thus, protectably covers the instep and helps stabilize the joint.

The pair of first wrap portions 26 extend between the top edge 16 and the pair of slits 22 a distance greater than the distance between the heel 14 and toes of the infant's foot. The pair of second wrap portions extend from the bottom edge 18 to the pair of slits 22 a distance which is less than the distance between the knee and heel of the infant to prevent interference with flexing of the knee joint.

As best shown in FIG. 3, the pad 12 has a resilient layer 32 and a flexible top cover sheet 34. The layer 32 may be of any flexible, resilient material sufficient to absorb pressure from a technician's hand during the fluid taking procedure. In the preferred embodiment, the resilient layer is formed of a synthetic foam material. The top cover sheet 34 is formed of a woven synthetic material having a surface texture for engagement with fastening strips of adhesive material such as Velcro ®. The top cover sheet is bonded to the resilient layer by any suitable method such as adhesive glues.

Affixed to each of the outer flaps 40, 44 of the pairs of first and second wrap portions is a fastening strip 36. Each fastening strip 36 has a synthetic material such as Velcro which is capable of adhering to the cover sheet when pressed together. Each fastening strip is affixed to the pad in a suitable manner such as by stitching 37.

The trauma protector is positioned for use by placing the pad 12 in an open position, as illustrated in FIG. 2, on the instep of the infant. The pad 12 is aligned so that the longitudinal axis of the elongated portion 24 is aligned parallel with a longitudinal axis of the infant's leg 13. The first pair of wrap portions 26 are positioned adjacent to the infant's foot and the pair of second wrap portions 28 are positioned adjacent to the infant's leg.

As shown in FIG. 2, the inner flap 38 of the pair of first wrap portions is folded over the sole of the infant's foot and the inner flap 42 of the pair of second wrap portions is folded over the back of the leg of the infant. The outer flaps 40 and 44 are then folded over the respective inner flaps 38 and 42 and fixed in position by engaging each fastening strip 36 with the cover sheet 34 of the pad. In this manner, the pair of slits 22 between the extending about the heel to provide access for the point of a lancet 48.

The elongated portion 24 extends over the instep and partially covers the ankle of the infant leaving the heel exposed by the opening 46. Thus, the movement of the ankle is restricted and less hand pressure is required to stabilize the infant's leg and foot during the procedure.

A support member 52 may be provided to add additional support to the ankle to prevent bending of the foot and to disperse the pressure exerted by the fingers of the technician such as shown in FIG. 5. The support member is formed of a stiff foam which is slightly resilient, yet stiff enough to maintain its shape under pressure. As shown in FIG. 4, the support member 52 has an arcuate upper surface 54, a flat bottom surface 56, and a pair of side surfaces 58 extending therebetween. The upper surface 54 has a radius of curvature generally equal to the radius of curvature formed by the cover sheet of the pad at theinstep and is adapted to be correspondingly received on the cover sheet of the pad 12 adjacent the instep of the leg. The bottom surface 56 is adapted to receive pressure from along the fingers of the technician as shown in FIG. 5.

Extending along the arcuate surface 54 is an attachment strip 60 of fastening material having a synthetic attachment material, such as Velcro, which will adhere to the cover sheet 34. The support member 52 is then placed in position in the instep formed in the pad formed by pressing the attachment strip 62 into the cover sheet, as shown in FIG. 5. Once assembled, the support member maintains the infant's foot and ankle in position. The inner and outer flaps are attached snugly enough about the leg to prevent The technician grasps the trauma protector, as best shown in FIG. 1, with the leg of the infant in the palm of the hand and the index finger extending around the heel and over the bottom of the infant's foot. A support member, though not shown in FIG. 1, may be used in this configuration. An alternative method of grasping is shown in FIG. 5, in which the technician's first two fingers are extended over the back of the infant's leg and the thumb extends over the foot.

It is, of course, within the scope of the invention to produce the apparatus in different sizes to accomodate larger children, adults or used in conjunction with other joints.

It will be further apparent to those skilled in the art that various modifications and changes may be made to the present invention without departing from the scope of the invention as defined in the appended claims. In particular, it is within the scope of the invention to have wrap portions extend from only one side of the elongated portion and to make those wrap portions sufficiently long to extend around and encircle the leg. Additionally, the pad may have rounded corners as shown in FIG. 3 or may be contoured to more properly conform to the shape of the infant's leg.

What is claimed is:

1. A trauma protector for protecting a foot of a human baby from trauma occuring when the foot is grasp by a hand of a technician during the injection or removal of fluid from a heel of the foot, the foot having an instep opposite from the heel and an angle which joins the foot to the lower leg portion of the baby, said trauma protector comprising:

a generally rectangular pad, said pad having a top, a bottom, said bottom being spaced apart and generally parallel to said top, an two spaced apart and generally parallel sides, said pad having an outer surface and an inner surface, said inner surface being generally smooth and continuous for contacting the foot of the baby, said pad having a pair of slits, one slit extending form one side to a first inner position short of a center line extending between said top and bottom of said pad, the other slit extending from the other side to a second inner position short of said center line, wherein slits are substantially aligned with each other and are substantially parallel to said top, said pad having a central portion between said inner positions of said slits extending along an axis defining an upper portion and a lower poriton, said upper portion extending from said axis to said top, said lower poriton extending from axis to said bottom, said upper portion having a first pair of wrap portions and said lower portion having a second pair of wrap portion, one wrap portion of each first and second pair of wrap portions extending an equal length along each respective slit;

means for securing one of said first air of wrap poritons to said upper portion when said first pair of wrap portions are wrapped with said one of said first wrap portions over another of said wrap portions about the lower leg portion of the baby;

means for securing one of said second pair of wrap portions to said lower portion when said second pair of wrap portions are wrapped with said one of said second pair of wrap portions over an other of said wrap portions about the foot of the baby, a support member demountably attached to an opposite side of said central portion of said pad for supporting said foot and absorbing pressure executed on said foot by said hand of said technician; and means for demountably attaching said support member to said pad;

wherein said slits register with the heel so that, with the foot extending substantailly perpendicular to the lower leg portion, the slits define an opening to provide access to the heel of the foot.

2. The trauma protector of claim 1, wherien said means for securing comprises a pair of substantially identical strips having hooks for engagement with said pad, one of said pair of strips extending outwardly from said one of said first wing portions and an other of said pair of strips extending from one of said second wrap portions.

3. The trauma protector of claim 1 wherein said pad has a resilient foam member and a smooth cover sheet affixed to said foam member.

4. The trauma protector of claim 1 wherein one of said pair of first wrap portions is an inner flap and an other one of said pair of first wrap portions is an outer flap, said outer flap being adapted to overlay said inner flap when said inner and outer flaps extend about said foot of said baby.

5. The trauma protector of claim 1 wherein one of said pair of second wrap portions is an inner flap and an other one of said pair of second wrap portions is an outer flap, said outer flap being adapted to overlay said inner flap when said inner and outer flaps extend about said lower leg portion of said baby.

6. The trauma protector of claim 1 wherein said means for demountably attaching said support member further comprises a strip formed of synthetic material which is adapted to adhere to said cover sheet when pressed on said pad.

7. The trauma protector of claim 6 wherein said support member further comprises a flat surface, a curved surface, and a pair of side surfaces extending therebetween, said curved surface adapted to abut said, .elongated surface adjacent said instep of said foot.

* * * * *